United States Patent [19]
Chatreaux et al.

[11] Patent Number: 5,968,939
[45] Date of Patent: Oct. 19, 1999

[54] AROMATIC DERIVATIVES SUBSTITUTED BY A RIBOSE, THEIR PREPARATION PROCESS AND THEIR USE AS MEDICAMENTS

[75] Inventors: Fabienne Chatreaux, Neuilly aur Marne; Michel Klich, Villemomble; Laurent Schio, Noisy le Sec, all of France

[73] Assignee: Hoechst Marion Roussel, France

[21] Appl. No.: 09/120,642

[22] Filed: Jul. 22, 1998

[30] Foreign Application Priority Data

Jul. 23, 1997 [FR] France .................................. 97 09352

[51] Int. Cl.⁶ ........................ A61K 31/495; C07D 405/14
[52] U.S. Cl. .................. 514/254; 514/228.2; 514/233.5; 514/422; 544/62; 544/151; 544/376; 548/525
[58] Field of Search ...................... 544/376, 151, 544/62; 548/525; 514/422, 254, 233.5, 228.2

[56] References Cited

U.S. PATENT DOCUMENTS 3,706,729 12/1972 Batcho et al. ....................... 260/210 R
5,412,104 5/1995 Afonso et al. ........................... 548/525

FOREIGN PATENT DOCUMENTS 467799 1/1969 Switzerland .

OTHER PUBLICATIONS

XP–002058225 Biochemistry, 35, pp. 5083–5092 Gormley et al., 1996.

XP–002058226 Journal Med. Chem., 1979, vol. 22, No. 2 pp. 158–168 Buckle et al.

Primary Examiner—Joseph K. McKane
Attorney, Agent, or Firm—Bierman, Muserlian and Lucas

[57] ABSTRACT

A subject of the invention is the compounds of formula (I):

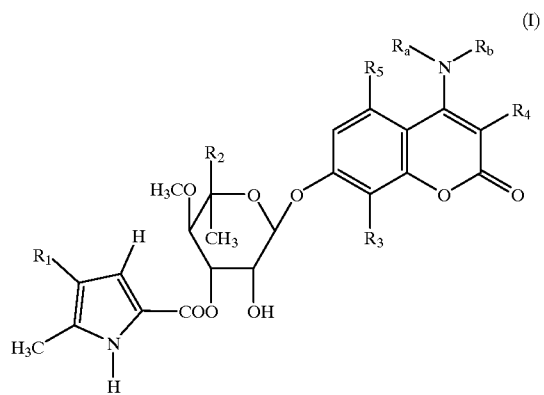

having antibiotic properties.

14 Claims, No Drawings

AROMATIC DERIVATIVES SUBSTITUTED BY A RIBOSE, THEIR PREPARATION PROCESS AND THEIR USE AS MEDICAMENTS

The present invention relates to new aromatic derivatives substituted by a ribose, their preparation process and their use as medicaments.

A subject of the invention is the compounds of formula (I):

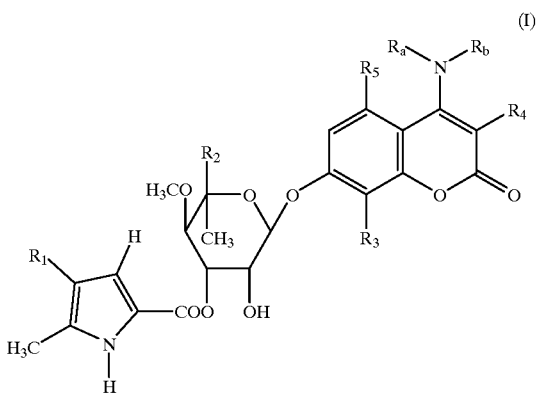

in which:
- $R_1$ represents a hydrogen or halogen atom,
- $R_2$ represents a hydrogen atom or an alkyl radical containing up to 4 carbon atoms,
- $R_3$ represents an alkyl radical containing up to 4 carbon atoms, or a halogen atom,
- $R_4$ represents a hydrogen atom, a halogen atom, a linear, branched or cyclic alkyl, alkenyl or alkynyl radical containing up to 12 carbon atoms,
- $R_5$ represents a hydrogen atom, an OH or O-alkyl radical, containing up to 12 carbon atoms,
- $R_a$ and $R_b$ identical or different represent a hydrogen atom, an alkyl radical containing up to 4 carbon atoms, either $R_a$ and $R_b$ form with the nitrogen atom to which they are linked a mono- or polycyclic heterocycle, optionally containing another heteroatom chosen from nitrogen, sulphur or oxygen, or $R_a$ and/or $R_b$ represent a radical:

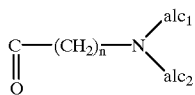

in which n is an integer varying from 0 to 6, $alk_1$ and $alk_2$ representing an alkyl radical containing up to 8 carbon atoms and their salts in all their possible stereoisomer forms as well as their mixtures.

As examples of salts there can also be mentioned the salts formed with the following acids: acetic, propionic, trifluoroacetic, maleic, tartaric, methanesulphonic, benzenesulphonic, p-toluenesulphonic, hydrochloric, hydrobromic, hydroiodic, sulphuric, phosphoric and especially stearic, ethylsuccinic or laurylsulphonic acids.

In the definition of the substituents:
- the alkyl, alkenyl or alkynyl radical is preferably a methyl, ethyl, propyl, isopropyl, n-butyl, isobutyl, terbutyl, decyl or dodecyl, vinyl, allyl, ethynyl, propynyl, cyclobutyl, cyclopentyl or cyclohexyl radical,
- the halogen is preferably fluorine or chlorine, or bromine,
- the aryl radical is preferably the phenyl radical,
- the heterocyclic radical is preferably the pyrrolyl, pyrrolidinyl, pyridyl, pyrazinyl, pyrimidyl, piperidinyl, piperazinyl, quinuclidinyl, oxazolyl, isoxazolyl, morpholinyl, indolyl, imidazolyl, benzimidazolyl, triazolyl, thiazolyl, azetidinyl, aziridinyl radical.

Among the preferred compounds of the invention, there can be quite particularly mentioned the compounds of formula (I) in which $R_1$ represents a hydrogen or fluorine atom, those in which $R_2$ represents a methyl radical or a hydrogen atom, those in which $R_3$ represents a methyl radical, a hydrogen or chlorine atom, those in which $R_4$ represents a hydrogen or chlorine atom, those in which $R_5$ represents a hydrogen atom, those in which $R_a$ and $R_b$ represent an alkyl radical containing up to 4 carbon atoms, and in particular a methyl radical, those in which $R_a$ and $R_b$ form with the nitrogen atom to which they are linked a heterocyclic radical optionally containing another heteroatom, and which can be optionally substituted, and in particular those in which $R_a$ and $R_b$ form together a

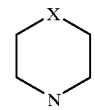

radical in which X represents an oxygen atom or an NH, or $NCH_3$ radical, the heterocyclic radical thus formed can be optionally substituted.

A more particular subject of the invention is the compounds the preparation of which is given hereafter in the experimental part and quite especially the compounds of Example 1 and 2.

The products of general formula (I) have a very good antibiotic activity on gram$^{3/4}$ bacteria such as staphylococci, streptococci, pneumococci enterococci, listeria, anaerobes.

The compounds of the invention can therefore be used as medicaments in the treatment of infections caused by susceptible germs and in particular, in that of staphylococcia, such as staphylococcal septicemias, malignant staphylococcia of the face or skin, pyodermatitis, septic or suppurating wounds, boils, anthrax, phlegmons, erysipelas and acne, staphylococcia such as acute primary or post-influenzal angina, bronchopneumonia, pulmonary suppuration, streptococcia such as acute angina, otitis, sinusitis, scarlet fever, pneumococcia such as pneumonia, bronchitis and diphtheria. The products of the present invention are also active against infections caused by germs such as Haemophilus influenzae.

Therefore a subject of the invention is the compounds of formula (I) as medicaments.

A more particular subject of the invention is as medicaments the compounds indicated above as preferred compounds.

A subject of the invention is also the pharmaceutical compositions containing at least one of the medicaments defined above as active ingredient.

These compositions can be administered by buccal, rectal, parenteral route or by local route as a topical application on the skin and mucous membranes, but the preferred administration route is the buccal or injectable route.

They can be solid or liquid and be presented in the pharmaceutical forms commonly used in human medicine, such as for example, plain or sugar-coated tablets, capsules, granules, suppositories, injectable preparations, ointments, creams, gels; they are prepared according to the usual methods. The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example apyrogenic sterile water.

The dose administered is variable accoring to the illness treated, the patient in question, the administration route and the product considered. It can be, for example, comprised between 50 mg and 3000 mg per day by oral or injectable route, in an adult for the preferred products.

A subject of the invention is also a process characterized in that a compound of formula (II):

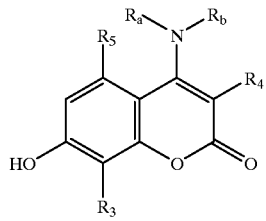

(II)

in which $R_3$, $R_4$, $R_5$, $R_a$ and $R_b$ retain their previous meaning, is subjected to the action of a compound of formula (III):

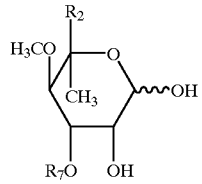

(III)

in which $R_2$ retains its previous meaning and $R_7$ represents a radical

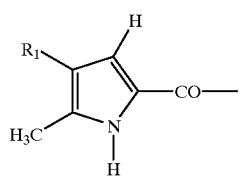

in which $R_1$ retains its previous meaning, in order to obtain the corresponding compound of formula (I) which is modified if desired.

A subject of the invention is also a variant of the process characterized in that a compound of formula (IV):

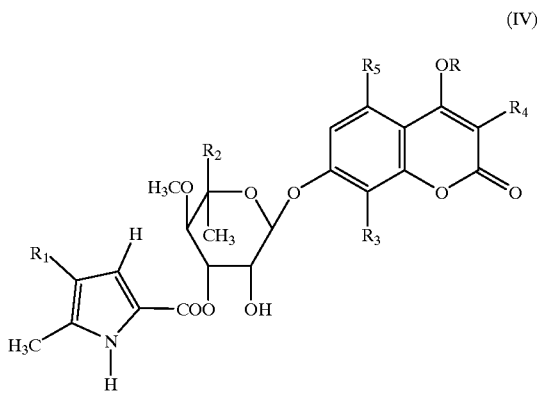

(IV)

in which $R_1$, $R_2$, $R_3$, $R_4$ and $R_5$ retain their previous meaning and R represents a parting group is subjected to the action of an amine

in which $R_a$ and $R_b$ retain their previous meaning in order to obtain the corresponding compound of formula (I) which is modified if desired.

The compounds of formulae (II) and (IV) are new products, their preparation is given hereafter in the experimental part, and are themselves a subject of the present invention.

The compounds of formula (II) can be prepared according to the process described in the experimental part, for example according to the following operating method:

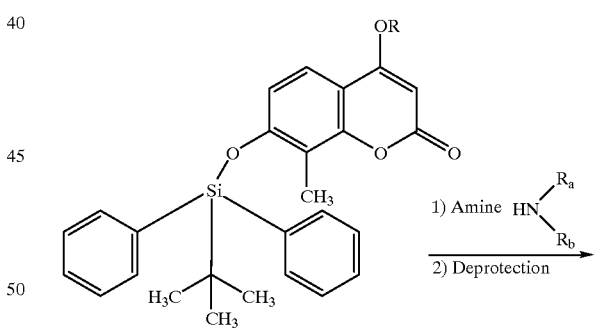

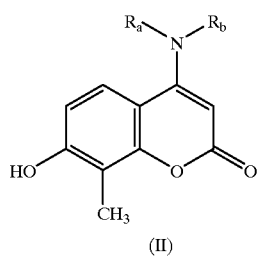

(II)

As parting groups R there can be mentioned the remainder of a tosylate, a mesylate, a triflate.

The compounds of formula (IV) can be prepared according to the processes described in the experimental part:

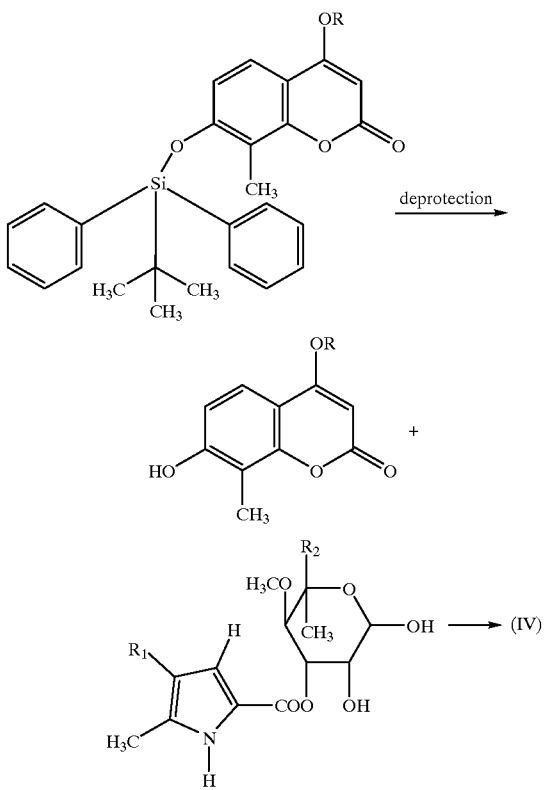

In the above R has the same value as the preceding parting groups.

EXAMPLE 1

(4-(dimethylamino)-8-methyl-2-oxo-2H-1-benzopyran-7-yl) 6-deoxy-5-C-methyl-4-O-methyl-3-O-(5-methyl-1H-pyrrol-2-yl) carbonyl) alpha-L-lyxo-hexopyranoside 5.3 ml of a 0.1 N solution of cobalt chloride in acetonitrile is introduced at 100° C. into a solution containing 210 mg of 7-(6-deoxy-5-C-methyl-4-O-methyl-alpha-L-lyxo-hexopyranosyl) oxy-4-(dimethylamino)-8-methyl-2H-1-benzopyran-2-one and 124 mg pyrrolic anhydride. Agitation is carried out at 100° C. for 15 minutes, the reaction medium is left to cool down and concentrated under reduced pressure. A product is obtained which is purified by chromatography on silica eluting with a methylene chloride-acetone mixture (80-20). 56.2 mg of sought product is obtained. rf=0.25, M.p.>300° C.

Preparation

7-[(6-deoxy-5-C-methyl-4-O-methyl-alpha-L-lyxo-hexopyranosyl) oxy]-4-(dimethylamino)-8-methyl-2H-1-benzopyran-2-one Stage A 7-[[(1,1-dimethylethyl)diphenylsilyl]oxy]-4-hydroxy-8-methyl-2H-1-benzopyran-2-one 85 ml of triethylamine is agitated in a suspension containing 50 g of 4,7-dihydroxy-8-methyl-2H-1-benzopyran-2-one and 400 ml of tetrahydrofuran. A solution of 76 ml of terbutyldiphenylchlorosilane in 50 ml of tetrahydrofuran is added. The reaction mixture is agitated for 20 hours, then it is poured into a buffer solution of sodium hydrogen phosphate. Extraction is carried out with ethyl acetate, the organic phase is washed with water, dried and brought to dryness. A product is obtained which is taken up in methanol, agitation is carried out for 4 hours, followed by separating, washing and drying. 84,5 g of sought product is obtained.

Stage B

7-[[(1,1-dimethylethyl)diphenylsilyl]oxy]-8-methyl-4-[[(trifluoromethyl)sulphonyl]oxy]-2H-1-benzopyran-2-one 7.3 ml of triethylamine is introduced at 0° C. into a suspension of 15 g of the product of Stage A in 150 ml of methylene chloride. A solution of 7.1 ml trifluoromethyl sulphonic anhydride and 7 ml of methylene chloride are added. The reaction mixture is maintained under agitation for 30 minutes at 0° C., then for 1 hour at ambient temperature. The reaction medium is poured into 150 ml of a 1M solution of sodium acid phosphate, followed by extraction with methylene chloride, washing, drying and concentrating under reduced pressure. A product is obatined which is chromatographed on silica eluting with a hexane-ethyl acetate mixture (8-2). In this way 17.1 g of sought product is obtained. rf=0.49.

Stage C 4-(dimethylamino)-7-hydroxy-8-methyl-2H-1-benzopyran-2-one 11.3 ml of a 0.6 M solution of dimethylamine in THF is introduced into a solution of 1.05 g of the product prepared in Stage B and 10 ml of THF. The reaction medium is maintained under agitation overnight. Nitrogen is bubbled through, the reaction is cooled down using an ice bath then 1.9 ml of n-tetrabutylammonium fluoride (1.1 M solution in THF) is poured in. Agitation is carried out for 15 minutes at OEC. The reaction medium is poured into 20 ml of a 1M solution of sodium acid phosphate. Extraction is carried out with methylene chloride. The organic phases are washed, dried and concentrated. A product is obtained which is taken up in methylethylketone, followed by separating, washing with methylethylketone and drying. The filtrate is concentrated, taken up in ethyl acetate, separated and dried. 350.4 mg of sought product is obtained. rf=0.18 methylene chloride/acetone (9-1).

Stage D

7-[(6-deoxy-5-C-methyl-4-O-methyl-alpha-L-lyxo-hexopyranosyl)oxy]-4-(dimethylamino)-8-methyl-2H-1-benzopyran-2-one 1.2 g of triphenylphosphine and 796 µl of DEAD (diethylazodicarboxylate) are introduced into a suspension containing 830 mg of the product of the previous stage and 804 mg of 6-deoxy-5-C-methyl-4-O-methyl-alpha-L-lyxo-hexopyranose and 20 ml of methylene chloride. Agitation is carried out for one hour at ambient temperature and two additions of 0.6 then 0.4 equivalents of triphenyl phosphine and DEAD are carried out at a one hour interval. Concentration is carried out followed by chromatography on silica eluting with a methylene chloride/acetone mixture (80-20). After treatment with acetone the sought product is obtained rf=0.29 (methylene chloride-acetone (6-4)).

EXAMPLE 2

(8-methyl-4-(4-methyl-1-piperazinyl)-2-oxo-2H-1-benzopyran-7-yl) 6-deoxy-5-C-methyl-4-O-methyl-3-O-(5-methyl-1H-pyrrol-2-yl)carbonyl)alpha-L-lyxo-hexopyranoside 354 mg of triphenylphosphine and 224 µl of DEAD are introduced into a dispersion containing 500 mg of 7-hydroxy-8-methyl-4-(4-methyl-1-piperazinyl)-2H-1-benzopyran-2-one and 370 mg of 6-deoxy-5-C-methyl-4-O-methyl-L-lyxohexopyranose 3-(5-methyl-1H-pyrrole-2-carboxylate). After reaction for 2 hours, 354 mg of triphenylphosphine and 224 µl of DEAD are added. Agitation is carried out for 2 hours and 283 mg of triphenylphosphine and 180 µl of DEAD are added. Agitation is carried out for another 2 hours, and 142 mg of triphenylphosphine and 90 µl of DEAD are added. Agitation is continued for 2 hours, followed by concentration and chromatography on silica, eluant MeOH—CH$_2$Cl$_2$ (5-95). rf=0.21. In this way 373 mg of sought product is isolated. M.p.=150° C.

Preparation 7-hydroxy-8-methyl-4-(4-methyl-1-piperazinyl)-2H-1-benzopyran-2-one

Stage A

7-[[(1,1-dimethylethyl)diphenylsilyl]oxy]-8-methyl-4-(4-methyl-1-piperazinyl)-2H-1-benzopyran-2-one 1.25 ml of N-methyl piperazine is added to a solution containing 2.53 g of 7-[[(1,1-dimethylethyl)diphenylsilyl] oxy]-8-methyl-4-[[(trifluoromethyl)sulphony]oxy]-2H-1-benzopyran-2-one and 22 ml of THF. The reaction medium is maintained under agitation for 1 hour, poured into a 1M aqueous solution of sodium acid phosphate, and extraction is carried out with ethyl acetate. The organic phases are combined, washed, dried and concentrated under reduced pressure. Chromatography is carried out on silica eluting with a methanol-methylene chloride mixture (6-94). 2.31 g of sought product is isolated. rf=0.3.

Stage B 7-hydroxy-8-methyl-4-(4-methyl-1-piperazinyl)-2H-1-benzopyran-2-one 5.10 ml of a 1.1 M solution of n-tetrabutyl ammonium fluoride is added at 0° C. to THF. The reaction medium is maintained under agitation for 1 hour at 0° C. and 270 µl of acetic acid is added, followed by concentrating, chromatography on silica eluting with a methanol-methylene chloride mixture 5-95 then 10-90, taking up in methylene chloride, separating and 0.88 g of product is isolated. rf=0.26 methanol-methylene chloride 10-90.

EXAMPLE 3

(4-(4,4-dimethylpiperazinium)-8-methyl-2-oxo-2H-1-benzopyran-7-yl)6-deoxy-5-C-methyl-4-O-methyl-3-O-(5-methyl-1H-pyrrol-2-yl)carbonyl)alpha-L-lyxo-hexopyranoside iodide 8.5 µl of iodomethane is added to a dispersion of 50 mg of the product of the preceding example in 1 ml of acetonitrile. The reaction mixture obtained is maintained under agitation at 60° C., cooled down and concentrated under reduced pressure. After taking up in methylene chloride and separation, 52 mg of sought product is obtained. M.p.=230° C.

EXAMPLE 4

N-(7-((6-deoxy-5-C-methyl-4-O-methyl-alpha-L-lyxo-hexopyranosyl) oxy)-8-methyl-2-oxo-2H-1-benzopyran-4-yl-2-(dimethylamino)acetamide5-methyl-1H-pyrrole-2-carboxylic-acid 3'-ester 152 mg of 2-(dimethylamino)-N-(7-hydroxy-8-methyl-2-oxo-2H-1-benzopyran-4-yl)acetamide, 106 mg of triphenylphosphine and 67 µl of DEAD are added to a dispersion containing 118 mg of 6-deoxy-5-C-methyl-4-O-methyl-alpha-L-lyxo-hexopyranose 5-methyl-1H-pyrrole-2-carboxylic acid ester and 3.5 ml of methylene chloride. The reaction medium is maintained under agitation for 2 hours at ambient temperature and another 106 mg of triphenylphosphine and 67 µl of DEAD are added. After an additional 2 hours of reaction, another 42 mg of triphenylphosphine and 27 µl of DEAD are added. Agitation is maintained for 2 hours and the product obtained is chromatographed, firstly eluting with a methanol-methylene chloride mixture (5-95) then with an acetone-methylene chloride mixture (20-80). In this way 72 mg of sought product is isolated. M.p.=260° C.

Preparation 2-(dimethylamino)-N-(7-hydroxy-8-methyl-2-oxo-2H-1-benzopyran-4-yl)acetamide Stage A 4-amino-7-[[[(1,1-dimethylethyl)diphenylsilyl]oxy]-8-methyl-2-oxo-2H-1-benzopyran-4-yl]-acetamide 783 mg of imidazole then 1.43 ml of tBuPh$_2$SiCl is added to a dispersion containing 1 g of 4-amino-7-hydroxy-8-methyl-2H-1-benzopyran-2-one and 25 ml of anhydrous DMF. The reaction medium is agitated for 16 hours at ambient temperature, poured into an aqueous solution (1M) of sodium acid phosphate and extraction is carried out with THF. The aqueous phase is decanted and extraction is carried out with ethyl acetate. The organic phases are combined, washed with water, dried and concentrated under reduced pressure. The product obtained is chromatographed on silica eluting with a methanol-methylene chloride mixture (5-95). The product obtained is taken up in ether and separated. 1.01 g of sought product is obtained. rf=0.33, methanol-methylene chloride (5-95).

Stage B 2-chloro-N-[7-[[(1,1-dimethylethyl)diphenylsilyl]oxy]-8-methyl-2-oxo-2H-1-benzopyran-4-yl]-acetamide 752 µl of TEA and 430 µl of chloroacetyl chloride is added at 0° C. to a solution containing 885 mg of the product of the preceding stage and 18 ml of THF. Agitation is carried out for 38 hours and the reaction medium is poured into an aqueous solution of sodium acid phosphate (1M) and extraction is carried out twice with ethyl acetate. The organic phases are combined, washed, dried and concentrated under reduced pressure. The product obtained is chromatographed on silica eluting with an ethyl acetate-methylene chloride mixture (2-98). In this way 453 mg of sought product is isolated.

Stage C 2-(dimethylamino)-N-(7-hydroxy-8-methyl-2-oxo-2H-1-benzopyran-4-yl)acetamide A few drops of dimethylamine are added at 0° C. to a solution containing 351 mg of the product of the preceding stage and 7 ml of THF. The reaction medium is maintained under agitation for 2 hours at ambient temperature and concentrated under reduced pressure. The residue obtained is impatsed in acetone and separation is carried out, followed by washing with methylene chloride, then with pentane. After drying, 110 mg of product is isolated. The filtrate is chromatographed on silica eluting with a methanol-methylene chloride mixture (5-95). In this way an additional 32 mg of sought product is isolated rf=0.27.

EXAMPLE 5

7-(6-deoxy-5-C-methyl-4-O-methyl-alpha-L-lyxo-hexopyranosyl)oxy)-8-methyl-4-(4-morpholinyl)-2H-1-benzopyran-2-one 5-methyl-1H-pyrrole-2-carboxylic acid -3'-ester By operating as previously starting from 387 mg of 7-hydroxy-8-methyl-4-(4-morpholinyl)-2H-1-benzopyran-2-one and 487 mg of 6-deoxy-5-C-methyl-4-O-methyl-L-lyxohexo-pyranose 3-(5-methyl-1H-pyrrole-2-carboxylate), 115.4 mg of sought product is obtained. M.p.>260° C.

EXAMPLE 6

7-((6-deoxy-5-C-methyl-4-O-methyl-alpha-L-lyxo-hexopyranosyl)oxy)-4-dimethylamino)-8-methyl-2H-1-benzopyran-2-one 4-fluoro-5-methyl-1H-pyrrole-2-carboxylic-acid 3'-ester 213 mg of 4-fluoro-5-methyl-1H-pyrrole-2-carboxylic acid then 182 mg of DMAP, then 233 μl of DIC are added to a dispersion containing 585 mg of 7-[(6-deoxy-5-C-methyl-4-O-methyl-alpha-L-lyxo-hexopyranosyl)oxy]-4-(dimethylamino)-8-methyl-2H-1-benzopyran-2-one and 15 ml of methylene chloride. Agitation is carried out for 14 hours at ambient temperature and 222 μl of DBU is added. Agitation is caried out for 2 hours at ambient temperature then the product obtained is chromatographed eluting with a methanol-methylene chloride mixture (5-95). The product obtained is taken up in acetone and separated. The product obtained is taken up in methanol and separated. 77 mg of sought product is isolated. M.p.>260° C.

EXAMPLE 7

7-((6-deoxy-5-C-methyl-4-O-methyl-alpha-L-lyxo-hexopyranosyl)oxy)-4-(2-dimethylamino) ethylmethylamino)-8-methyl-2H-1-benzopyran-2-one 5-methyl-1H-pyrrole-2-carboxylic acid-3'-ester The product was prepared by operating as previously, rf=0.15, $CH_2Cl_2$—MeOH—$NH_3$ (92-8-0.5).

EXAMPLE 8

7-((6-deoxy-5-C-methyl-4-O-methyl-alpha-L-lyxo-hexopyranosyl)oxy)-8-methyl-4-(1-piperazinyl)-2H-1-benzopyran-2-one 5-methyl-1H-pyrrole-2-carboxylic acid-3'-ester M.p.=190≈200° C.

EXAMPLE 9

8-methyl-4-(4-methyl-1-piperazinyl)-2-oxo-2H-1-(3-chlorobenzo pyran)-7-yl 6-deoxy 5-methyl-4-O-methyl-3-O-((5-methyl-1H-pyrrol-2-yl)carbonyl)-alpha-L-lyxo-hexopyranoside.

By operating as previously starting from 3-chloro-7-hydroxy-8-methyl-4-(4-methyl-1-piperazinyl)-2H-1-benzopyran-2-one, the sought product is obtained. M.p.=145° C.

EXAMPLE 10

7-((6-deoxy-5-C-methyl-4-O-methyl-alpha-L-lyxo-hexopyranosyl)oxy)-4-(4-ethyl-1-piperazinyl)-8-methyl-2H-1-benzopyran-2-one 5-methyl-1H-pyrrole-2-carboxylic acid-3'-ester 374 mg of 7-hydroxy 8-methyl-4-(4-ethyl-1-piperazinyl) 2H-1-benzopyran-2-one, 424 mg of 6-deoxy-5-C-methyl-4-O-methyl-L-lyxohexopyranose 3-(5-methyl-1H-pyrrole-2-carboxylate) and 408 mg of triphenylphosphine are suspended in 12 ml of methylene chloride. 275 μl of DEAD is added. Agitation is carried out for 2 hours at ambient temperature and 408 mg of triphenyl-phosphine and 275 μl of DEAD are added. Agitation is carried out for 1 hour 45 minutes and 170 mg of triphenylphosphine and 113 μl of DEAD are added. The product obtained is chromatographed eluting with a methylene chloride-isopropanol mixture (9-1). The product is poured into 30 ml of a molar solution of sodium dihydrogen phosphate and extraction is carried out with methylene chloride, followed by washing with a saturated solution of sodium chloride. The organic phases are combined and dried over magnesium sulphate. 2.61 g of product is isolated which is chromatographed on silica eluting with a methylene chloride-methanol mixture (90-10). The fraction with rf=0.10 is isolated, 350 mg of product is obtained which is impasted in acetonitrile, the product obtained is separated, the filtrate is brought to dryness, followed by taking up with acetonitrile, separating and combining with the first fraction obtained. In this way 170 mg of sought product is isolated. M.p.=246≈248° C.

EXAMPLE 11

7-((6-deoxy-5-C-methyl-4-O-methyl-alpha-L-lyxo-hexopyranosyl)oxy)-8-methyl-4-(4-(2-pyrimidyl)-1-piperazinyl)-2H-1-benzopyran-2-one 5-methyl-1H-pyrrole-2-carboxylic acid-3'-ester By operating as previously starting with 7-hydroxy-8-methyl-4-[4-(2-pyrimidinyl)-1-piperazinyl]-2H-1-benzopyran-2-one, the sought product was obtained. rf=0.25, methylene chloride-isopropanol (97-3).

By operating as previously, the following products were obtained:

EXAMPLE 12

(4-(dimethylamino)-8-methyl-2-oxo-2H-1-benzopyran-7-yl 6-deoxy-4-O-methyl-3-O-((5-methyl-1H-pyrrol-2-yl)carbonyl)-alpha-L-mannopyranoside M.p.=225° C.

EXAMPLE 13

(8-methyl-4-(4-morpholinyl)-2-oxo-2H-1-benzopyran-7-yl 6-deoxy-4-O-methyl-3-O-((5-methyl-1H-pyrrol-2-yl)carbonyl)-alpha-L-mannopyranoside M.p.=190° C.

EXAMPLE 14

(8-methyl-4-(4-methyl-1-piperazinyl)-2-oxo-2H-1-benzopyran-7-yl 6-deoxy-4-O-methyl-3-O-((5-methyl-1H-pyrrol-2-yl)carbonyl)-alpha-L-mannopyranoside rf=0.31 acetone-ethyl acetate-water (5-4-1).

EXAMPLE 15

4,4-dimethyl-piperazinium-1-yl)-8-methyl-2-oxo-2H-1-benzopyran-7-yl 6-deoxy-4-O-methyl-3-O-((5-methyl-1H-pyrrol-2-yl)carbonyl)-alpha-L-mannopyranoside iodide By subjecting the product of the previous example to the action of methyl iodide, the sought product was obtained. rf=0 acetone-ethyl acetate-water (5-4-1).

EXAMPLE 16

7-((6-deoxy-5-C-methyl-4-O-methyl-alpha-L-lyxo-hexopyranosyl)oxy)-8-methyl-4-(3-methyl-1-piperazinyl)-2H-1-benzopyran-2-one 5-methyl-1H-pyrrole-2-carboxylic acid-3'-ester By operating as previously, the sought product was obtained. M.p.=205° C.

EXAMPLE 17

7-((6-deoxy-5-C-methyl-4-O-methyl-alpha-L-lyxo-hexopyranosyl)oxy)-8-methyl-4-(4-(2-piridinyl)-1-piperazinyl)-2H-1-benzopyran-2-one 5-methyl-1H-pyrrole-2-carboxylic acid-3'-ester By operating as previously, the sought product was obtained. M.p.=228≈230° C.

EXAMPLE 18

7-((6-deoxy-5-C-methyl-4-O-methyl-alpha-L-lyxo-hexopyranosyl)oxy)-4-(4-dimetylamino)-1-piperidinyl)-8-methyl-2H-1-benzopyran-2-one 5-methyl-1H-pyrrole-2-carboxylic acid-3'-ester 0.8 mmole of 7-[(6-deoxy-5-C-methyl-4-O-methyl-alpha-L-lyxo-hexopyranosyl)oxy]-8-methyl-4-[[(4-methylphenyl)sulphonyl]oxy]-2H-1-benzopyran-2-one 5-methyl-1H-pyrrole-2-carboxylic acid-3'-ester is added at ambient temperature to a solution containing 2 mmole of 4-dimethylamino-1-piperidine, in 2.5 ml of THF. Agitation is carried out for 2 hours. The reaction medium is poured into a saturated solution of sodium acid phosphate (1M). Extraction is carried out with ethyl acetate, followed by drying, concentrating and 87 mg of product is obtained to which 2 ml of acetonitrile is added; a product is obtained which is separated and dried. In this way 58 mg of product is obtained. M.p.=190° C.

Preparation

7-[(6-deoxy-5-C-methyl-4-O-methyl-alpha-L-lyxo-hexopyranosyl)oxy]-8-methyl-4-[[(4-methylphenyl)sulphonyl]oxy]-2H-1-benzopyran-2-one 5-methyl-1H-pyrrole-2-carboxylic acid-3'-ester Stage A 7-(hydroxy-8-methyl-4-[[(4-methylphenyl)sulphonyl]oxy]-2H-1-benzopyran-2-one 3.5 g of tosyl chloride is added at 0° C., to a solution containing 3.50 g of 4,7-dihydroxy 8-methyl-2H-1-benzopyran-2-one and 25 ml of pyridine. Agitation is carried out for 2 hours at 0° C., the reaction medium is poured into a 1.2N aqueous solution of hydrochloric acid. Extraction is carried out with ethyl acetate, the organic phases are combined, dried and concentrated under reduced pressure. The product obtained is chromatographed on silica eluting with an acetone-methylene chloride mixture 5-95 and 3.88 g of a product is isolated which is impasted in ether and separated. The sought product is obtained. M.p.=206° C.

Stage B

7-[(6-deoxy-5-C-methyl-4-O-methyl-alpha-L-lyxo-hexopyranosyl)oxy]-8-methyl-4-[[(4-methylphenyl)sulphonyl]oxy]-2H-1-benzopyran-2-one 5-methyl-1H-pyrrole-2-carboxylic acid-3'-ester 1.4 g of triphenylphosphine and 886 µl of DEAD are added to a solution of 1.87 g of the product of the preceding stage, 2 g of 6-deoxy-5-C-methyl-4-O-methyl-L-lyxo-hexopyranose 3,3-(5-methyl)-1H-pyrrole-2-carboxylate) and 50ml of methylene chloride. Agitation is carried out at ambient temperature for 1 hour, 0.5 equivalents of triphenylphosphine and DEAD are added, agitation is carried out for 45 minutes, another 0.25 equivalents of triphenylphosphine and DEAD are added. Agitation is carried out for 30 minutes, followed by concentrating. After filtering, the product obtained is chromatographed on silica eluting with a methylene chloride-acetate mixture (95-5). 1.43 g of sought product is obtained. rf=0.25.

EXAMPLE 19

7-((6-deoxy-5-C-methyl-4-O-methyl-alpha-L-lyxo-hexanopyranosyl)oxy)-4-(4-hydroxy-1-piperidinyl)-8-methyl-2H-1-benzopyran-2-one 5-methyl-1H-pyrrole-2-carboxylic acid-3'-ester 101.15 mg of 4-hydroxy 1-piperidine is added to a solution containing 216 mg of 7-[(6-deoxy-5-C-methyl-4-O-methyl-alpha-L-lyxo-hexopyranosyl)oxy]-8-methyl-4-[[(4-methylphenyl)sulphonyl]oxy]-2H-1-benzopyran-2-one 5-methyl-1H-pyrrole-2-carboxylic acid-3'-ester and 5 ml of THF. Agitation is carried out for 1 hour. A 1M solution of sodium acid phosphate. Extraction is carried out with ethyl acetate followed by drying and concentrating. A product is obtained which is chromatographed on silica eluting with a methylene chloride-acetone mixture (6-4). After concentrating, 53 mg of sought product is obtained. M.p.=230° C.

EXAMPLE 20

(S) 7-((6-deoxy-5-C-methyl-4-O-methylalpha-L-lyxo-hexopyranosyl)oxy)-4-[2-(hydroxymethyl)-1-pyrrolidinyl]-8-methyl-2H-1-benzopyran-2-one 5-methyl-1H-pyrrole-2-carboxylic acid-3'-ester 240 µl of 2-pyrrolidine methanol is introduced into a solution of 607 mg of 7-((6-deoxy-5-C-methyl-4-O-methylalpha-L-lyxo-hexopyranosyl)oxy)-4-[[(4-methylphenyl)sulphonyl]oxy]-2H-1-benzopyran-2-one 5-methyl-1H-pyrrole-2-carboxylic acid-3'-ester and 5 ml of THF. Agitation is carried out at ambient temperature for 30 minutes. The reaction medium is poured into 15 ml of a 1M solution of $NaH_2PO_4$, followed by extraction with ethyl acetate, drying and concentrating. A product is obtained which is chromatographed on silica eluting with a methylene chloride-acetone mixture (7-3). After concentrating, 173 mg of product is obtained which is taken up in acetonitrile. After separating and drying, 110 mg of sought product is obtained. M.p.>240° C.

EXAMPLE 21

7-((6-deoxy-5-C-methyl-4-O-methylalpha-L-lyxo-hexopyranosyl)oxy)-4-(2-hydroxymethyl)-4-morpholinyl]-8-methyl-2H-1-benzopyran-2-one 5-methyl-1H-pyrrole-2-carboxylic acid-3'-ester By operating as previously starting with 7-[(6-deoxy-5-C-methyl-4-O-methyl-alpha-L-lyxo-hexopyranosyl)oxy]-8-methyl-4-[[(4-(methylphenyl)-sulphonyl]oxy]-8-methyl-2H-1-benzopyran-2-one 5-methyl1H-pyrrole-2-carboxylic acid-3'-ester and 2-(hydroxymethyl)-4-morpholine, the sought product is obtained. M.p.=260° C.

EXAMPLE 22

7-((6-deoxy-5-C-methyl-4-O-methyl-alpha-L-lyxo-hexopyranosyl)oxy)-8-methyl-4-(methylamino)-2H-1-benzopyran-2-one 5-methyl-1H-pyrrole-2-carboxylic acid-3'-ester By operating as previously starting with 500 mg of 7-[(6-deoxy-5-C-methyl-4-O-methyl-alpha-L-lyxohexopyranosyl)oxy]-8-methyl-4-[[(4-methylphenyl)
sulphonyl]oxy]-2H-1-benzopyran-2-one 5-methyl-1H-
pyrrole-2-carboxylic acid-3'-ester and methylamine, the
sought product was obtained. rf=0.27 methylene chloride-
isopropanol (9-1).

EXAMPLE 23

7-((6-deoxy-5-C-methyl-4-O-methyl-alpha-L-lyxo-
hexopyranosyl)oxy)-4-(2-((dimethylamino)methyl)-
4-morpholinyl]-8-methyl-2H-1-benzopyran-2-one 5-
methyl-1H-pyrrole-2-carboxylic acid-3'-ester By operating as previously starting with
2-(dimethylamino)methyl-4-morpholine and 7-[(6-deoxy-5-
C-methyl-4-O-methyl-alpha-L-lyxo-hexopyranosyl)oxy]-8-
methyl-4-[[(4-methyl phenyl)sulphonyl]oxy]-2H-1-
benzopyran-2-one 5-methyl-1H-pyrrole-2-carboxylic acid-
3'-ester, the sought product was obtained. rf=0.18 methylene
chloride-ethanol (8-2).

By operating as previously the following products were
obtained:

EXAMPLE 24

7-((6-deoxy-5-C-methyl-4-O-methyl-alpha-L-lyxo-
hexopyranosyl)oxy)-4-(3,5-dimethyl-1-piperidinyl)-
8-methyl-2H-1-benzopyran-2-one 5-methyl-1H-
pyrrole-2-carboxylic acid-3'-ester M.p.=260≈262°
C.

EXAMPLE 25

7-[(6-deoxy-5-C-methyl-4-O-methyl-alpha-L-lyxo-
hexopyranosyl)oxy]-4-(4-(2-hydroxyethyl)1-
piperazinyl)-8-methyl-2H-1-benzopyran-2-one 5-
methyl-1H-pyrrole-2-carboxylic acid-3'-ester M.p.=
230≈232° C.

EXAMPLE 26

(trans)7-[(6-deoxy-5-C-methyl-4-O-methyl-alpha-L-
lyxo-hexopyranosyl)oxy]-4-(2,5-dimethyl-1-
piperazinyl)-8-methyl-2H-1-benzopyran-2-one 5-
methyl-1H-pyrrole-2-carboxylic acid-3'-ester
(mixture of diastereoisomers) rf=0.1 methylene
chloride-ethanol (90-10).

Examples of Pharmaceutical Compositions

Tablets were prepared containing:

| Product of Example 1 | 150 mg |
|---|---|
| Excipient q.s.f. | 1 g |

Detail of excipient: starch, talc, magnesium stearate

| Product of Example 2 | 150 mg |
|---|---|
| Excipient q.s.f. | 1 g |

Detail of excipient: starch, talc, magnesium stearate.
Injectable solutions were also prepared from the salts.

Pharmacological Study of the Products of the Invention

A—Method of dilutions in liquid medium

A series of tubes are prepared in which the same quantity
of sterile nutritive medium is distributed. Increasing quantities of the product to be studied are distributed into each
tube, then each tube is sown with a bacterial strain. After
incubation for 24 hours in a heating chamber at 37° C., the
growth inhibition is evaluated by transillumination, which
allows the minimal inhibitory concentrations (M.I.C.) to be
determined, expressed in micrograms/cm$^3$.

On the following strains:

| S. aureus | 011HT3 |
|---|---|
| S. aureus | 011UC4 |
| S. aureus | 011HT28 |
| S. epidermidis | 012GO20 |
| S. aureus | 011CB20 |
| S. aureus | 011HT26 |
| S. epidermidis | 012GO39 |
| S. epidermidis | 012HI1 |
| S. pyogenes | 02A1UC1 |

The following resultats were obtained:

0.04<MIC<5

B—Inhibition of gyrase B

The products are inhibitors of gyrase B; the dose at 50%
DNA supercoiling is less than 5:g/ml.

We claim:
1. A compound selected from the group consisting of a
compound of the formula

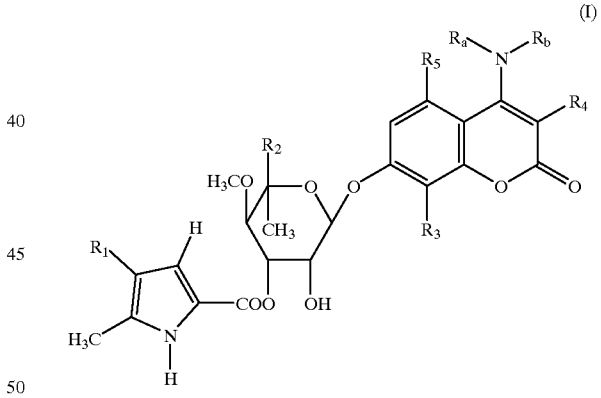

in which:

$R_1$ is hydrogen or halogen, $R_2$ is hydrogen or an alkyl of 1 to 4 carbon atoms, $R_3$ is alkyl of 1 to 4 carbon atoms, or a halogen atom, $R_4$ is selected from the group consisting of hydrogen,
halogen, alkyl, alkenyl and alkynyl of up to 12 carbon
atoms, $R_5$ is selected from the group consisting of hydrogen, OH
and alkoxy of, up to 12 carbon atoms, $R_a$ and $R_b$ are individually selected from the group
consisting of hydrogen, alkyl of 1 to 4 carbon atoms, either $R_a$ and $R_b$ form with the nitrogen atom to which they are linked a mono- or polycyclic heterocycle, optionally having another heteroatom chosen from nitrogen, sulphur or oxygen, or $R_a$ and/or $R_b$ are

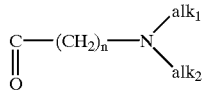

in which n is an integer from 0 to 6, $alk_1$ and $alk_2$ are alkyl of 1 to 8 carbon atoms and their salts in all their possible stereoisomer forms as well as their mixtures.

2. The compounds of formula (I) as defined in claim 1, in which $R_1$ is a hydrogen or fluorine atom.

3. A compound of claim 1, in which $R_2$ is methyl or hydrogen.

4. The compounds of formula (I) as defined in claim 1, in which $R_3$ represents a methyl, a hydrogen or chlorine atom.

5. The compounds of formula (I) as defined in claim 1, in which $R_4$ represents a hydrogen or chlorine atom.

6. The compounds of formula (I) as defined in in which $R_5$ represents a hydrogen atom.

7. A compound of claim 1, in which $R_a$ and $R_b$ are alkyl of 1 to 4 carbon atoms.

8. The compounds of formula (I) as defined in claim 7 in which $R_a$ and $R_b$ represent a methyl.

9. The compounds of formula (I) as defined in any one of claims 1 to 6, in which $R_a$ and $R_b$ form with the nitrogen atom to which they are linked a heterocyclic optionally having another heteroatom.

10. A compound of claim 9 in which $R_a$ and $R_b$ together form

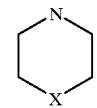

wherein X is oxygen or NH or $NCH_3$.

11. The compound of claim 1 selected from the group consisting of
(4-dimethylamino-8-methyl-2-oxo-2H-1-benzopyran-7-yl)-6-deoxy-5-C-methyl-4-0-methyl3-0-((5-methyl-1H-pyrrol-2-yl)-carbonyl)alpha-L-lyxo-hexopyranoside and
(8-methyl-4-(4-methyl-1-piperazinyl)-2-oxo-2H-1-benzopyran-7-yl)-6-deoxy-5-C-methyl-4-O-methyl-3-O-((5-methyl-1H-pyrrol-2-yl)carbonyl)-alpha-L-lyxo-hexopyranoside.

12. An antibiotic composition comprising an antibiotically effective amount of a compound of claim 1 and an inert pharmaceutical carrier.

13. A method of treating bacterial infections in warm-blooded animals comprising administering to warm-blooded animals a bacterially effective amount of a compound of claim 1.

14. The method of claim 13 wherein the compound is selected from the group consisting of [4-dimethylamino-8-methyl-2-oxo-2H-1-benzopyran-7-yl]-6-deoxy-5-C-methyl-4-0-methyl-3-0-[(5-methyl-1H-pyrrol-2-yl)-carbonyl]-α-L-lyxo-hexopyranoside and [8-methyl-4-(4-methyl-1-piperazinyl)-2-oxo-2H-1-benzopyran-7-yl]-6-deoxy-5-C-methyl-4-O-methyl3-O-[(5-methyl-1H-pyrrol-2-yl)-carbonyl]-α-L-lyxo-hexopyranoside.

\* \* \* \* \*